United States Patent
Wang et al.

(10) Patent No.: US 9,226,982 B2
(45) Date of Patent: Jan. 5, 2016

(54) GALL BLADDER IMAGING AGENT AND ITS PREPARATION METHOD

(71) Applicant: INSTITUTE OF NUCLEAR ENERGY RESEARCH ATOMIC ENERGY COUNCIL, EXECUTIVE YUAN, Taoyuan County (TW)

(72) Inventors: Mei-Hui Wang, Taoyuan County (TW); Hung-Man Yu, Taoyuan County (TW); Chuan-Yi Chien, Taoyuan County (TW); Ping-Yen Wang, Taoyuan County (TW); Wuu-Jyh Lin, Taoyuan County (TW); Kun-Liang Lin, Taoyuan County (TW); Jen-Tsung Wang, Taoyuan County (TW)

(73) Assignee: INSTITUTE OF NUCLEAR ENERGY RESEARCH ATOMIC ENERGY COUNCIL, EXECUTIVE YUAN, Taoyuan County (TW)

(*) Notice: Subject to any disclaimer, the term of this patent is extended or adjusted under 35 U.S.C. 154(b) by 89 days.

(21) Appl. No.: 14/143,602

(22) Filed: Dec. 30, 2013

(65) Prior Publication Data
US 2014/0186262 A1 Jul. 3, 2014

(30) Foreign Application Priority Data
Dec. 28, 2012 (TW) .............................. 101150985 A
Oct. 29, 2013 (TW) .............................. 102139109 A

(51) Int. Cl.
*A61K 51/00* (2006.01)
*A61M 36/14* (2006.01)
*A61K 51/04* (2006.01)

(52) U.S. Cl.
CPC ......... *A61K 51/0491* (2013.01); *A61K 51/0478* (2013.01)

(58) Field of Classification Search
None
See application file for complete search history.

(56) References Cited

U.S. PATENT DOCUMENTS

| 8,142,759 B2 | 3/2012 | Wang et al. |
| 8,435,491 B2 | 5/2013 | Wang et al. |
| 8,552,163 B2 | 10/2013 | Lee et al. |
| 2011/0097264 A1 | 4/2011 | Wang et al. |
| 2012/0107236 A1 | 5/2012 | Wang et al. |

OTHER PUBLICATIONS

Lee Reiko, Wang Mei-Hui, Lin Wuu-Jyh, Lee Yuan Chuan, "New and More Efficient Multivalent Glyco-Ligands for Asialoglycoprotein Receptor of Mammalian Hepatocytes",Bioorganic Medicinal Chem 19(8):2494-2500, 2011.
Yu Hung Man, Wang Mei-Hui, Chen Jezon T, Lin Wuu-Jyh,"Labelling of Peptide Derivative with In-111 for Receptor Imaging", J LabelledCompd and Radiopharm 53, 417, 2010.

*Primary Examiner* — Michael G Hartley
*Assistant Examiner* — Melissa Perreira
(74) *Attorney, Agent, or Firm* — WPAT, PC; Justin King

(57) ABSTRACT

A novel gall bladder image agent which includes a radiolabelled MAG3-tri-galactosamine, and its preparation method, which includes reacting mercaptoacetyltriglycine (MAG3)-tri-galactosamine, SnF2 and Tc-99m in the presence of a phosphate buffer solution (at pH of from 10.0~12.0) to obtain Tc-99m-MAG3-tri-galactosamine, when the MAG3-tri-galactosamine is MAG3-DCM-Lys(Gah-GalNAc)3 (where DCM represents a dicarboxymethyl group, and Gah represents a glycine-aminohexyl group), it obtains a labelling yield of at least 90%, and its specific radioactivity is at least $7.0 \times 10^9$ Bq/mg.

10 Claims, 10 Drawing Sheets

GALL BLADDER IMAGING AGENT AND ITS PREPARATION METHOD

BACKGROUND OF THE INVENTION

1. Field of Invention

The present invention mainly provides a gall bladder imaging agent and its preparation method.

2. Related Art

Tc-99m-di-isopropyl iminodiacetic acid (DISIDA) is a gall bladder imaging agent in clinical use, which is an analog of bilirubin and has a similar metabolic pathway in human body. Tc-99m-DISIDA can accumulate at a gall bladder and is mostly used to estimate whether a cystic duct is unobstructed to diagnose an infant with biliary atresia in an early period. However, Tc-99m-DISIDA is not suitable for patients with liver dysfunctions. Patients with liver dysfunctions absorb Tc-99m DISIDA drugs very slowly and drugs cannot accumulate at the gall bladder easily, so it is very difficult to observe whether bile transportation is unobstructed with this agent. Patients with liver dysfunctions need to seek other methods.

Asialoglycoprotein receptor (ASGPR) is a liver specific receptor and has specific binding to glycopeptides or glycoproteins with galactose (Gal) or acetylgalactosamine (GalNAc) at an end. These glycopeptides and glycoproteins enter a liver cell through endocytosis of a liver receptor and eventually exits through a bile duct, and accordingly are theoretically applicable for scanning and imaging of gall bladders, and are used to observe the presence of symptoms of biliary atresia. It has been found through earlier researches in our laboratory that ASGPR disappears only when all liver cells have turned into liver cancer cells. Otherwise, as long as there are normal liver cells, ASGPR is present to absorb glycopeptides or glycoproteins with Gal or GalNAc at an end. Therefore, it is technically feasible for an ASGPR biological imaging marker (that is, glycopeptides or glycoproteins with Gal or GalNAc at an end) to serve as a gall bladder imaging agent.

Conventional technetium-99m-diethylenetriamine pentaacetic acid-galactosyl-albumin (Tc-99m-DTPA-GSA) can be used in liver imaging. Albumin is used as a backbone, on which an unpredictable number of galactosyls and DTPA are connected. The number of connected DTPA is different by batch as the fabrication process cannot be controlled. Therefore, the labelling amount of technetium-99m also changes with the DTPA, and accordingly the specific radioactivity is very different in each time of preparation. Also, the metabolic rate of Tc-99m-DTPA-GSA in the liver is very slow and it is difficult to observe the absorption of the gall bladder, so that Tc-99m-DTPA-GSA is not suitable for use as a gall bladder imaging agent.

Tyrosine-glutamyl-glutamic acid (YEE) and tyrosine-aspartyl-aspartic acid (YDD) are first proposed by Lee et al. (1983). Tyrosine-glutamyl-glutamyl-glutamic acid (YEEE) is an improved invention by Chen et al. (ROC Patent TW1240002, 2000). The binding force between double-chain galactose amino peptide proposed by Lee et al. in 1983 and a liver cell is 1000 times as large as that of single-chain galactose amino peptide. The binding force between triple-chain galactose amino peptide and a liver cell is $10^6$ times as large as that of sing-chain galactose amino peptide. Our laboratory has synthesized DTPA-hexa-lactose with a single lysine derivative earlier, which has very high specific radioactivity with the In-111 label and has a very desirable effect of accumulation at the liver in animal experiments. However, our animal experiments have shown that In-111-DTPA-hexa-lactose stays at the liver very stably for at least half an hour, and it is actually not easy to observe changes of absorption of the gall bladder in the entire imaging process. Therefore, In-111-DTPA-hexa-lactose is suitable for use in remaining liver function test or measurement of remaining liver after liver resection, but is not very suitable for use as a gall bladder imaging agent.

SUMMARY OF THE INVENTION

In view of this, to solve the above problem, we use a tri-galactose chain instead. Because of a small molecular weight, a high metabolic rate, and very high binding capacity with a liver cell, the tri-galactose chain might be a very good choice. The present invention is the optimal marker for use as a gall bladder imaging agent that is finally chosen after a series of preparation, combination, and label tests of Tc-99m, DTPA, $MAG_3$, tri-galactosamine, and hexa-lactose. The present invention relates to the novel gall bladder imaging agent and its preparation method for the reuse thereof in the industry.

The precursor of a Tc-99m label can usually be saved for a long term through lyophilization. When demands of hospitals rise, radioactive isotopes are then added in the lyophilized precursor to complete label reaction in an instant dissolution manner, which facilitates marketing. In medical applications, the usage of Tc-99m is very high. With most hospitals being equipped with a $^{99}Mo/^{99}mTc$ generator, Tc-99m is readily available and has a short half-life (6 hours), and is therefore very suitable for use in diagnosis. As can be seen from a conventional technetium-99m-DTPA-galactose-albumin in the prior art, the DTPA-galactose-albumin and Tc-99m has very good binding. Theoretically, DTPA-tri-galactosamine and DTPA-hexa-lactose should also work. However, the results of the embodiments show that the precursor DTPA-tri-galactosamine of the present application and DTPA-hexa-lactose label Tc-99m do not have a high labelling yield. Therefore, we do not chelate DTPA and Tc-99m, but further use mercaptoacetyltriglycine (mercaptoacetyltriglycine) ($MAG_3$) instead as a bifunctional chelate. It is already known that $MAG_3$ and Tc-99m can be chelated for use as a kidney imaging agent, because it has 3 anilide nitrogens and sulfhydryl (these form a $N_3S$ structure) to effectively capture Tc-99m, and also still has one COOH to be bonded to a peptide amino through an anilide bond, so that it can be used as a bifunctional chelate for Tc-99m. Although an ideal radio label is one mole of polymer carbohydrate chain bonded to one mole of radioactive isotope, difficulties are encountered in practice, and even carbohydrate chains with similar structures also have quite different radio chemical characteristics. By bonding a polymer carbohydrate chain with $MAG_3$, the $MAG_3$-hexa-lactose fails to reach a satisfactory labelling yield. However, $MAG_3$-tri-galactosamine can react at the room temperature for 15 minutes without any purification to reach a high specific radioactivity. Also, the metabolic rate of $MAG_3$-tri-galactosamine at the liver is very high, and it is metabolized to the gall bladder in 15 minutes, so that the imaging time for a patient is clearly shortened. Also, Tc-99m is a common nuclide used in hospitals and has a short half-life and very low toxicity, which is suitable for commercial promotion and use.

Therefore, the present invention provides a preparation method of Tc-99m-$MAG_3$-tri-galactosamine, which comprises the following steps:

(1) performing glycosidation reaction of acetylated galactose amine and 6-(benzyloxycarbonyl glycine amino) hexanol and performing deprotection of an acetoxy on the galactose amine using alkali, so as to obtain 6-(benzyloxycarbonyl glycine amino) hexyl galactose amine;

(2) performing hydrogenolysis reaction on the 6-(benzyloxycarbonyl glycine amino) hexyl galactose amine to obtain 6-(glycine amino) hexyl galactose amine;

(3) reacting 6-(glycine amino) hexyl galactose amine and nitrilotriacetic acid protected by benzyloxycarbonyl amine to obtain tri-galactosamine;

(4) performing amide bonding on the obtained tri-galactosamine and mercaptoacetyltriglycine ($MAG_3$) to cause reaction, so as to obtain $MAG_3$-tri-galactosamine; and (5) performing radio-labelling on the obtained $MAG_3$-tri-galactosamine and Tc-99m, so as to obtain Tc-99m-$MAG_3$-tri-galactosamine.

In the preparation method according to the present invention, the mercaptoacetyltriglycine ($MAG_3$) used in the foregoing step (4) is to use a precursor of S-benzoyl thio-acetyl triglycine, and to perform deprotection of benzoyl before reaction.

In the preparation method according to the present invention, the foregoing step (5) is performed in the presence of $SnHal_2$ (Hal represents chlorine or fluorine, and preferably fluorine) serving as a reductant and a buffer solution at pH of from 10.0~12.0.

In the preparation method according to the present invention, the buffer solution is a phosphate buffer solution or ammonium acetate ($NH_4OAc$).

In the preparation method according to the present invention, step (5) is further performed in the presence of a stabilizer, and the stabilizer is preferably tartaric acid.

The present invention further provides Tc-99m-$MAG_3$-tri-galactosamine prepared by using the foregoing preparation method, which is used as a gall bladder imaging agent and especially as a gall bladder imaging agent for diagnosing biliary atresia.

Tc-99m-$MAG_3$-tri-galactosamine in the present invention is also used as an imaging agent in a quantitative analysis method in SPECT/CT in vivo molecular imaging.

Tc-99m-$MAG_3$-tri-galactosamine in the present invention can achieve a labelling yield of at least 90%, and the specific radioactivity is at least $7.0 \times 10^9$ Bq/mg.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Figure 1:
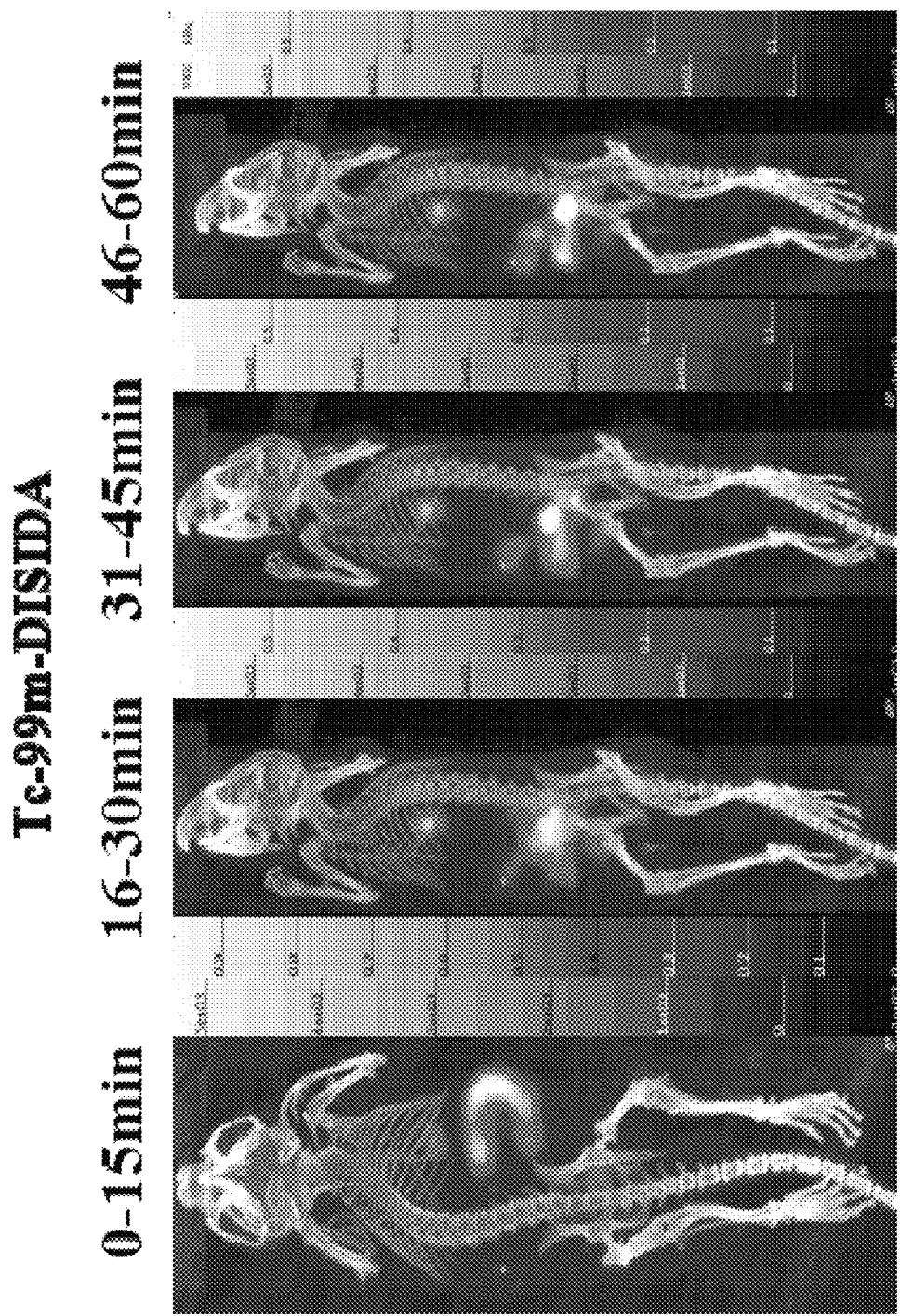
FIG. 1 is an imaging picture of Tc-99m DISIDA nano SPECT/CT.

As for features and examples of the present invention, a preferred embodiment will be illustrated in detail with reference to the accompanying drawings.

Embodiment 1

Design of Liver Target Drug of the Present Application

The design of the liver target drug of the present application uses $N^\epsilon$-benzyloxycarbonyl-N,N-bis-(carboxymethyl)-L-lysine (Z-DCM-Lys) as a new basic structure to connect in string 6-aminohexyl β-N-acetylgalactosamine (ah-GalNAc), 6-N-glycineaminohexyl β-N-acetylgalactosamine (Gah-GalNAc) or 6-aminohexyl β-lactoside (ah-Lac) to form tri-glycopeptide. As the binding strength of lactose amine chain to ASGPR is smaller than that of a galactose amine chain, if a lactose amine chain is connected in string, 2 molecules of tri-lactose chains are further connected in string with L-aspartic acid (aspartic acid) or glutamic acid. For example, 2 molecules of α-dicarboxylmethyl-L-lysine-tris(aminohexyl β-lactoside ($\epsilon$-Z-α-DCM-Lys(ah-Lac)$_3$) are connected through $N^\alpha$-(trifluoroacetaminohexanoyl)-L-aspartic acid (TFA-AHA-Asp), and after the trifluoroacetyl radical is removed, AHA-Asp[DCM-Lys(ah-Lac)$_3$]$_2$ (hexa-lactoside) is formed.

Embodiment 2

Analysis on Binding Strength Between Carbohydrate Chain Peptide and Mice Liver Cell The binding strength between carbohydrate chain peptide and a mice liver cell uses Eu-asialo-orosomucoid (Eu-ASOR) as a reference substance and compares whether carbohydrate chain peptides such as DCM-Lys(ah-GalNAc)$_3$, DCM-Lys(Gah-GalNAc)$_3$, DCM-Lys(ah-Lac)$_3$, and AHA-Asp[DCM-Lys (ah-Lac)$_3$]$_2$ have larger binding capacity to a mice liver cell than Eu-ASOR. $IC_{50}$ (50% inhibitory concentration) represents the binding capacity. Smaller $IC_{50}$ represents larger binding capacity. Mice liver cells are purchased from Lonza biotechnology company in State of Maryland, which are placed and cultivated on a 24-well plate in advance. Reaction takes place at each well. Add (1) 10 nM of Eu-ASOR, (2) a liver cell basic culture medium added with 5 mM of ammonium chloride, and (3) 1 μM~0.8 nM of 5 carbohydrate chain peptides of different concentrations, respectively. Perform oscillating culture for 1 hours. Use an ammonium-chloride-containing liver cell base culture medium to wash away substances that are not bonded to liver cells. Perform time-resolved fluorescence analysis, namely, add an enhancer (15 μM of β-naphthoyl trifluoroacetone, 50 μM of tri-n-octylphosphine oxide, 0.1M of potassium hydrogen phthalate, and 0.1% of Triton X-100 in 0.1M of acetic acid, pH of 3.2). The enhancer forms an Eu chelate with $Eu^{3+}$ and emits light of 615 nm when energized by 340 nm. The logarithmic value of the concentration of carbohydrate chain peptide is taken as X-axis, and the emitted fluorescence value is taken as the Y-axis. The fluorescence value when no glycopeptide is added is set to be 100%, and $IC_{50}$ values of the carbohydrate chain peptides are calculated accordingly. See Table 1, as can be known from the data, the binding between AHA-Asp

[DCM-Lys(ah-Lac)₃]₂ and ASGPR can reach the same binding strength as YEE and YDD. However, the binding between DCM-Lys(Gah-GalNAc)₃ and ASGPR is 10 times as large as the binding strength of YEE and YDD.

TABLE 1

Comparison of binding strength between carbohydrate chains and mice liver cell

| Compound | IC50 (nM) |
| --- | --- |
| YEE(ahGalNAc)₃ | 10 nM |
| YDD(GahGalNAc)₃ | 10 nM |
| DCM-Lys(ahGalNAc)₃ | 10 nM |
| DCM-Lys(GahGalNAc)₃ | 1 nM |
| AHA-Asp[DCM-Lys(ahLac)₃]₂ | 10 nM |

Embodiment 3

Synthesis of Tri-Galactosamine

Figure 2:
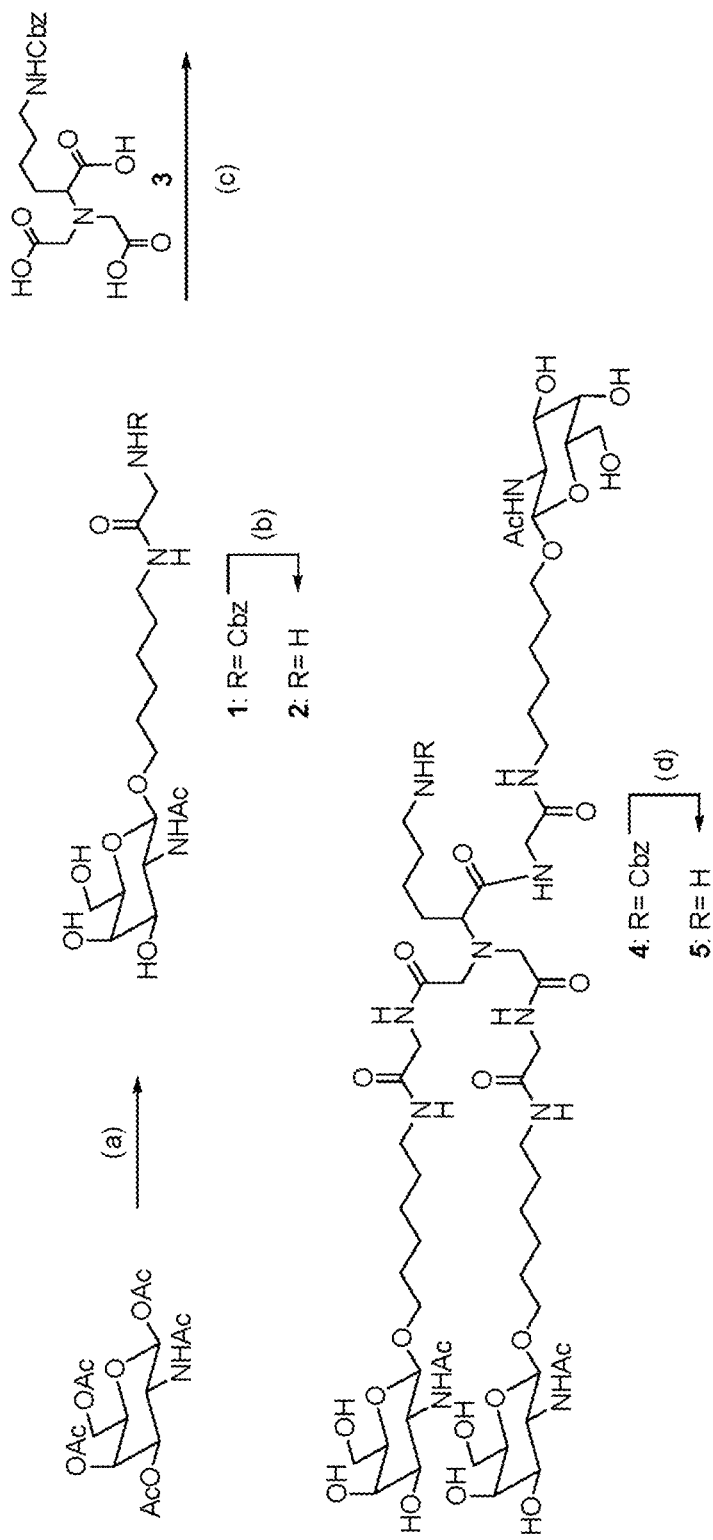
FIG. 2 is a flow chart of synthesizing tri-galactosamine.

See FIG. 2 for the preparation process. Tri-galactosamine is labeled as product 5. First, perform glycosidation reaction on galactose amine acetylated in advance and 6-(benzyloxycarbonyl glycine amino) hexanol under the catalysis by caBF$_3$OEt$_2$. Next, the acetal protection group of the hydroxyl on galactose amine is removed using sodium methoxide to obtain compound 1. The two-step synthesis yield is 46%. The central configuration of mutarotation and isomerism of the product is confirmed through hydrogen nuclear magnetic resonance spectroscopy, and through the signals on the spectrogram, the chemical offset is at the position of 4.37 ppm, the coupling constant is $J_{1,2}$=8.4 Hz, it can be confirmed that the configuration of compound 1 is β-type. Perform hydrogenolysis reaction on compound 1 to remove the benzyloxycarbonyl protection group easily to obtain compound 2. Subsequently, compound 2 is introduced, through amine bonds, into the tri-lactose backbone of nitrilotriacetic acid protected by benzyloxycarbonyl amino to obtain compound 4, and the yield is 89%. Next, similarly, Perform hydrogenolysis reaction in the air under the condition of Pd/C and hydrogen balloon to remove the benzyloxycarbonyl protection group to obtain compound 5 whose amine groups are exposed. Its analysis report is as follows: IR (KBr) 3410, 3196, 1654, 1547 cm$^{-1}$; $^1$H NMR (D$_2$O, 300 MHz) 4.28 (d, J=8.1 Hz, 3H), 3.81-2.62 (m, 43H), 1.86 (s, 9H), 1.60-1.01 (m, 30H); $^{13}$C NMR (D$_2$O, 75 MHz) 175.16, 174.52, 171.01, 101.76, 75.20, 71.17, 70.39, 67.94, 65.30, 61.09, 55.66, 52.60, 42.44, 39.70, 39.56, 28.67, 28.53, 25.84, 24.91, 22.81, 22.42; and ESI-MS (m/z) 671.10 [M+2H]$^{2+}$ and 1340.69 [M+H]$^+$.

Embodiment 4

Synthesis of MAG$_3$-Tri-Galactosamine

Figure 5:
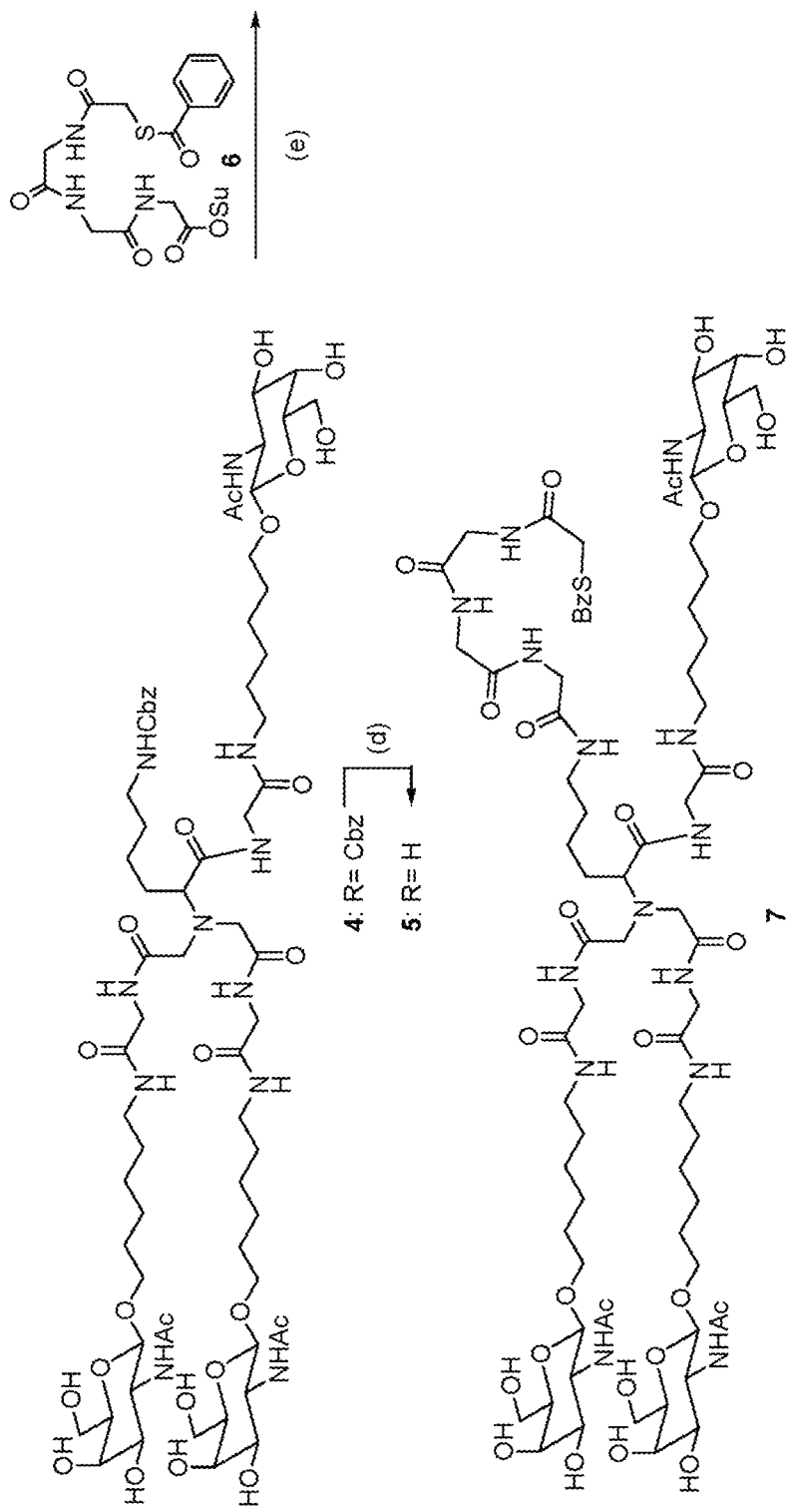
FIG. 5 is a flow chart of synthesizing $MAG_3$-tri-galactosamine.

See FIG. 5 for the preparation process. The amino group exposed on triple-chain galactose amine and the carboxyl on S-benzoyl thioacetamide triglycine (S-Bz-MAG$_3$) are coupled. The S-Bz-MAG$_3$ is synthesized referring to the published documents. Next, activate S-Bz-MAG$_3$ through performing benzoyl deprotection under the reaction condition of DCC/HOSu. Then, add tri-galactosamine and 4-dimethylaminopyridine obtained in Embodiment 3, and perform amide bonding to form the precursor compound MAG$_3$-tri-galactosamine, and the yield is 60%. The structures of all compounds are confirmed through IR, ESI-MS and hydrogen, carbon nuclear magnetic resonance spectroscopy. After the purity of compound 7 is confirmed, when the purity is greater than 98%, radio-labelling can be performed. The analysis report of the compound MAG$_3$-tri-galactosamine is as follows: IR (KBr) 3410, 3196, 1654 cm$^{-1}$. $^1$H NMR (D$_2$O, 300 MHz) 7.86~7.38 (m, 5H), 4.28 (d, J=8.1 Hz, 3H), 3.90~3.20 (m, 42H), 3.06~2.98 (m, 9H), 1.86 (s, 9H), 1.60~1.01 (m, 30H); $^{13}$C NMR (D$_2$O, 75 MHz) 175.16, 174.52, 171.01, 101.76, 75.20, 71.17, 70.39, 67.94, 65.30, 61.09, 55.66, 52.60, 42.44, 39.70, 39.56, 28.67, 28.53, 25.84, 24.91, 22.81, 22.42; and ESI-MS (m/z) 845.44 [M+2H]$^{2+}$ and 1690.75 [M+H]$^+$.

Embodiment 5

Radio-Labelling Method of Tc-99m MAG$_3$-Tri-Galactosamine

See Table 2 for the radio chemical label condition of Tc-99m MAG$_3$-tri-galactosamine. The label reaction condition includes changing the type of the buffer solution, the pH value, the proportions of Na$^{99m}$TcO$_4$ and MAG$_3$-tri-galactosamine, the type and amount of the reductant SnCl$_2$ or SnF$_2$.H$_2$O, the type of the stabilizer, the reaction temperature, and the like. The optimal conditions of radio-labelling not only need to consider the radio-labelling yield, which is usually higher than 90%, but also need to ensure that the specific radioactivity is as high as possible. As can be seen from Table 2, for the radio-labelling of Tc-99m-MAG$_3$-tri-galactosamine, the optimal conditions are 5 ug of MAG$_3$-tri-galactosamine, the radioactivity being Na$^{99m}$TcO$_4$ (1 mCi=6× 10$^{-17}$ Mole) of 5 mCi, 3 ug of SnF$_2$, 0.2 M of phosphate buffer solution (pH of 11), the room temperature, and reaction lasting 15 minutes. In such a manner, the radio-labelling yield is 97%, and the specific activity is 3.7×10$^{10}$ Bq/mg.

TABLE 2

Analysis experiment of radio-labelling condition and radio chemical purity of Tc-99m-MAG$_3$-tri-galactosamine

| Buffer | pH | MAG$_3$-tri-galactosamine | Na$^{99m}$TcO$_4$ (mCi of Tc-99m) | Reductant | Stabilizer | Temperature | RCP (%) |
| --- | --- | --- | --- | --- | --- | --- | --- |
| 0.2M NH$_4$OAc | 4 | 10 ug | 1 mCi | SnCl$_2$ 1 ug | 7 ug/uL tartaric acid | Room temperature | 4 |
| 0.2M NH$_4$OAc | 8 | 10 ug | 1 mCi | SnCl$_2$ 1 ug | 7 ug/uL tartaric acid | Room temperature | 69 |
| 0.2M NH$_4$OAc | 7.5 | 10 ug | 1 mCi | SnCl$_2$ 1 ug | 7 ug/uL tartaric acid | Room temperature | 76 |

TABLE 2-continued

Analysis experiment of radio-labelling condition and radio chemical purity of Tc-99m-MAG$_3$-tri-galactosamine

| Buffer | pH | MAG$_3$-tri-galactosamine | Na$^{99m}$TcO$_4$ (mCi of Tc-99m) | Reductant | Stabilizer | Temperature | RCP (%) |
|---|---|---|---|---|---|---|---|
| 0.2M NH$_4$OAc | 7.5 | 10 ug | 1 mCi | SnF$_2$ 1 ug | 7 ug/uL tartaric acid | Room temperature | 85 |
| 0.2M phosphate | 11 | 10 ug | 1 mCi | SnF$_2$ 1 ug | 7 ug/uL tartaric acid | Room temperature | 85 |
| 0.2M phosphate | 11 | 10 ug | 1 mCi | SnF$_2$ 1 ug | 0 ug/uL tartaric acid | Room temperature | 86 |
| 0.2M phosphate | 11 | 10 ug | 1 mCi | SnF$_2$ 1 ug | 1 ug/uL tartaric acid | Room temperature | 87 |
| 0.2M phosphate | 11 | 10 ug | 1 mCi | SnF$_2$ 1 ug | 7 ug/uL tartaric acid | Room temperature | 86 |
| 0.2M phosphate | 11 | 10 ug | 1 mCi | SnF$_2$ 1 ug | 35 ug/uL tartaric acid | Room temperature | 78 |
| 0.2M phosphate | 11 | 10 ug | 1 mCi | SnF$_2$ 1 ug | 0 | 60° C. 1 h | 78 |
| 0.2M phosphate | 11 | 30 ug | 1 mCi | SnF$_2$ 1 ug | 0 | 60° C. 1 h | 77 |
| 0.2M phosphate | 11 | 50 ug | 1 mCi | SnF$_2$ 1 ug | 0 | 60° C. 1 h | 77 |
| 0.2M phosphate | 11 | 10 ug | 1 mCi | SnF$_2$ 1 ug | 0 | room temperature 30 min | 94 |
| 0.2M phosphate | 11 | 10 ug | 1 mCi | SnF$_2$ 1 ug | 0 | 60° C. 30 min | 93 |
| 0.2M phosphate | 11 | 10 ug | 1 mCi | SnF$_2$ 1 ug | 0 | 60° C. 1 h | 78 |
| 0.2M phosphate | 11 | 10 ug | 1 mCi | SnF$_2$ 1 ug | 0 ug ascorbic acid | Room temperature | 93 |
| 0.2M phosphate | 11 | 10 ug | 1 mCi | SnF$_2$ 1 ug | 1 ug ascorbic acid | Room temperature | 94 |
| 0.2M phosphate | 11 | 10 ug | 1 mCi | SnF$_2$ 1 ug | 2 ug ascorbic acid | Room temperature | 79 |
| 0.2M phosphate | 11 | 10 ug | 1 mCi | SnF$_2$ 1 ug | 5 ug ascorbic acid | Room temperature | 42 |
| 0.2M phosphate | 11 | 10 ug | 1 mCi | SnF$_2$ 1 ug | 10 ug ascorbic acid | Room temperature | 56 |
| 0.2M phosphate | 11 | 0.1 ug | 1 mCi | SnF$_2$ 1 ug | 0 | Room temperature | 63 |
| 0.2M phosphate | 11 | 0.5 ug | 1 mCi | SnF$_2$ 1 ug | 0 | Room temperature | 75 |
| 0.2M phosphate | 11 | 1 ug | 1 mCi | SnF$_2$ 1 ug | 0 | Room temperature | 91 |
| 0.2M phosphate | 11 | 5 ug | 1 mCi | SnF$_2$ 1 ug | 0 | Room temperature | 92 |
| 0.2M phosphate | 11 | 5 ug | 5 mCi | SnF$_2$ 1 ug | 0 | Room temperature | 97 |
| 0.2M phosphate | 4 | 1 ug | 0.5 mCi | SnF$_2$ 1 ug | 0 | Room temperature | 12 |
| 0.2M phosphate | 5 | 1 ug | 0.5 mCi | SnF$_2$ 1 ug | 0 | Room temperature | 10 |
| 0.2M phosphate | 6 | 1 ug | 0.5 mCi | SnF$_2$ 1 ug | 0 | Room temperature | 3 |
| 0.2M phosphate | 7 | 1 ug | 0.5 mCi | SnF$_2$ 1 ug | 0 | Room temperature | 3 |
| 0.2M phosphate | 8 | 1 ug | 0.5 mCi | SnF$_2$ 1 ug | 0 | Room temperature | 3 |
| 0.2M phosphate | 9 | 1 ug | 0.5 mCi | SnF$_2$ 1 ug | 0 | Room temperature | 5 |
| 0.2M phosphate | 10 | 1 ug | 0.5 mCi | SnF$_2$ 1 ug | 0 | Room temperature | 50 |
| 0.2M phosphate | 11 | 1 ug | 0.5 mCi | SnF$_2$ 1 ug | 0 | Room temperature | 89 |

Comparison Example 1

Synthesis of Tri-Lactose

Figure 3:
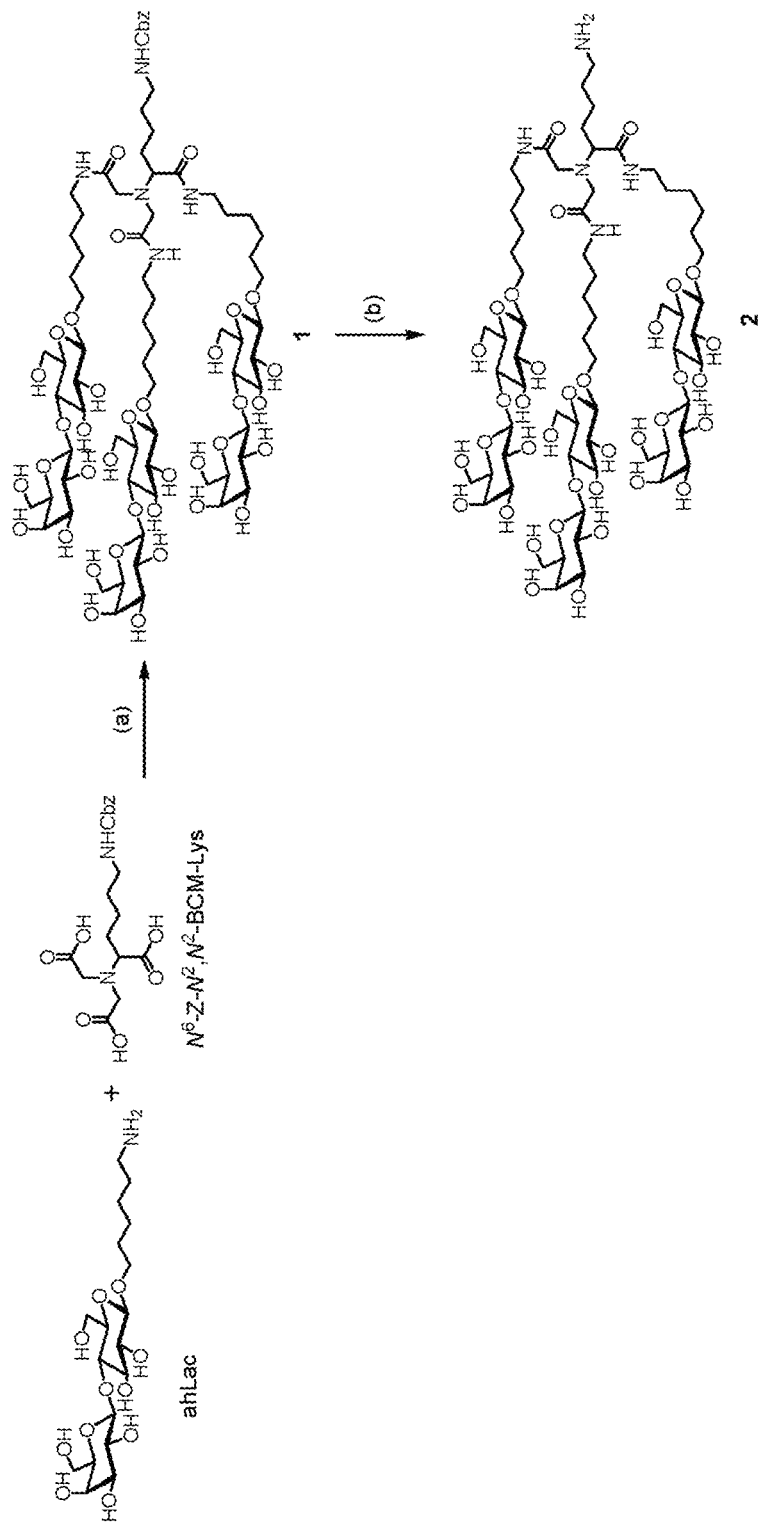
FIG. 3 is a flow chart of synthesizing tri-lactose.

See FIG. 3 for the synthesis and preparation process of tri-lactose. The step of obtaining tri-lactose is as follows: Add hydroxyl benzotriazole (HOBt, 500.0 mg, 3.69 mmol) and N,N-diisopropylethylaminee (DIPEA, 0.61 mL, 3.69 mmol) to 6-aminohexyl group-β-lactoside (ahLac, 1.61 g, 3.65 mmol) and $N^6$-benzyloxycarbonyl-$N^2$,$N^2$-bis-(carboxymethyl)-L-lysine ($N^6$—Z—$N^2$,$N^2$—BCM-Lys, 381 mg, 0.965 mmol) in DMF (24 mL). Add 1-Ethyl-3-(3-dimethylaminopropyl)carbodiimide (EDCI, 709 mg, 3.70 mmol) during ice bath. Perform reaction for 30 minutes in ice bath and move it to the nitrogen atmosphere at the room temperature to react overnight (about 15 hours). After the reaction ends, the solution is slightly yellowish. Under intense stirring, add aether (100 mL) and stir for 5~10 minutes. Place it still for 10 minutes and take the supernatant using a burette. Then, react the remaining yellowish colloid at the wall and bottom of the bottle. Perform ultrasonic oscillation washing with aether (30 mL) once. Take away the solution in the reaction bottle and perform high vacuum drying. Perform purification with an automatic fast preparative separation system. Perform reverse column chromatography (RP-18). The detection wavelength is set to be double wavelengths of 214 and 254 nm. Perform gradient elution on the mobile phase with methanol/water (methanol proportion is 40% to 60%) at the flow speed of 26 milliliters per minute for 15 min. After the separation and chromatography, perform collection at the product region and perform decompression and concentration (water bath at the temperature of 50° C.). Next, perform high vacuum drying to obtain the white solid tri-lactose backbone product (1358 mg), where the yield is 84%. Perform hydrogenolysis reaction to easily remove the benzyloxycarbonyl protection group. The compound analysis data is:

$C_{64}H_{117}N_5O_{36}$; TLC RP-18 (MeOH/1% TFA=5:5) Rf=0.76; $^1$H NMR (300 MHz, $D_2O$) δ 4.31 (3H, d, J=6.9 Hz), 4.29 (3H, d, J=6.9 Hz), 3.84~3.72 (9H, m), 3.67~3.28 (31H, m), 3.19~3.05 (12H, m), 2.83 (1H, t, J=6.9 Hz), 2.62 (2H, t, J=7.2 Hz), 1.49~1.30 (16H, m), 1.20 (14H, br); 13C NMR (75 MHz, $D_2O$) δ 174.40, 173.35, 103.08, 102.20, 78.54, 75.50, 74.91, 74.62, 72.98, 72.66, 71.09, 70.68, 68.69, 66.37, 61.17, 60.24, 55.96, 39.91, 39.32, 39.17, 29.30, 29.09, 28.84, 28.44, 26.01, 24.89, 24.83, 23.09; and ESI-HRMS: calcd for 766.87. found: m/z 767.22 $[M+2H]^{+2}$.

Comparison Example 2

Synthesis of Hexa-Lactose

Figure 4:
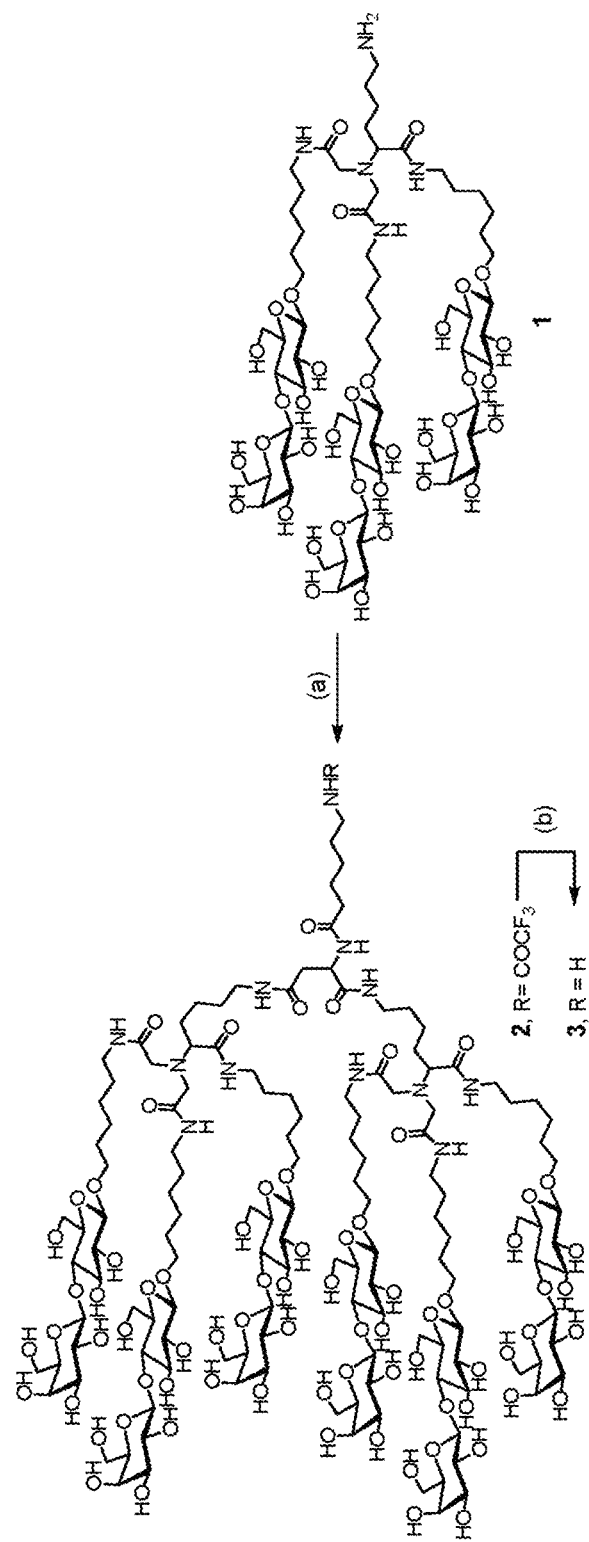
FIG. 4 is a flow chart of synthesizing hexa-lactose.

See FIG. 4 for the synthesis and preparation process of hexa-lactose. The steps of obtaining hexa-lactose are as follows: Add hydroxyl benzotriazole (HOBt, 105 mg, 0.69 mmol) and N,N-diisopropylethylaminee (DIPEA, 115 μL, 0.69 mmol) to N-(trifluoroacetaminohexanoyl) aspartic acid (94 mg, 0.28 mmol) and tri-lactose (1056 mg, 0.69 mmol) obtained in Comparison example 1 in the DMF (9 mL). Add 1-Ethyl-3-(3-dimethylaminopropyl)carbodiimide (EDCI, 132 mg, 0.69 mmol) during ice bath. Perform reaction for 30 minutes at the ice bath and move it to the nitrogen atmosphere at the room temperature to react about 6 hours. After the reaction ends, the solution is slightly yellowish. Under intense stirring, add aether (90 mL) and stir for 5~10 minutes. Place it still for 10 minutes and take the supernatant using a burette. React the remaining yellowish colloid at the wall and bottom of the bottle. Perform ultrasonic oscillation washing with aether (30 mL) once. Take away the solution in the reaction bottle and perform high vacuum drying. With an automatic fast preparative separation system, adopt reverse column chromatography (RP-18, methanol proportion 40% to 60%). After separation and chromatography, perform collection at the product region and perform decompression and concentration (water bath at the temperature of 50° C.). Next, perform high vacuum drying to obtain the white solid hexa-lactose backbone product (HexaLac-NHTFA, 841 mg), where the yield is 90%. Next, dissolve the white solid in triethylamine/alcohol/water (volume ratio 1:1:8, 16 mL), and stir the same at the room temperature overnight (about 18 hours). After the reaction is completed, perform decompression, concentration, and drying. Add methanol (about 20 mL) and through ultrasonic oscillation (5 minutes), white solid is separated out and is then sucked to a centrifugal tube. Perform centrifugal separation at 3000 rpm (revolutions per minute) for minutes. Suck the upper-layer methanol supernatant using a burette and move the bottom-layer solid to the high vacuum system drying, so as to obtain the compound hexa-lactose (HexaLac, 745 mg) with the benzyloxycarbonyl protection group removed, where the yield is 92%. The analysis data of the compound: $^1$H NMR (300 MHz, $D_2O$) δ 4.47 (1H, t, J=6.6 Hz), 4.31 (6H, d, J=7.5 Hz), 4.29 (6H, d, J=7.2 Hz), 3.83~3.71 (19H, m), 3.67~3.32 (66H, m), 3.26~2.99 (36H, m), 2.53 (1H, dd, J=14.7, 5.7 Hz), 2.42 (1H, dd, J=14.7, 8.7 Hz), 2.13 (2H, t, J=6.9 Hz), 1.46~1.35 (36H, m), 1.19 (30H, br); and ESI-HRMS: calcd for 1092.5404. found: m/z 1092.5397 $[M+3H]^{+3}$.

Comparison Example 3

Synthesis of $MAG_3$-Hexa-Lactose

Figure 6:
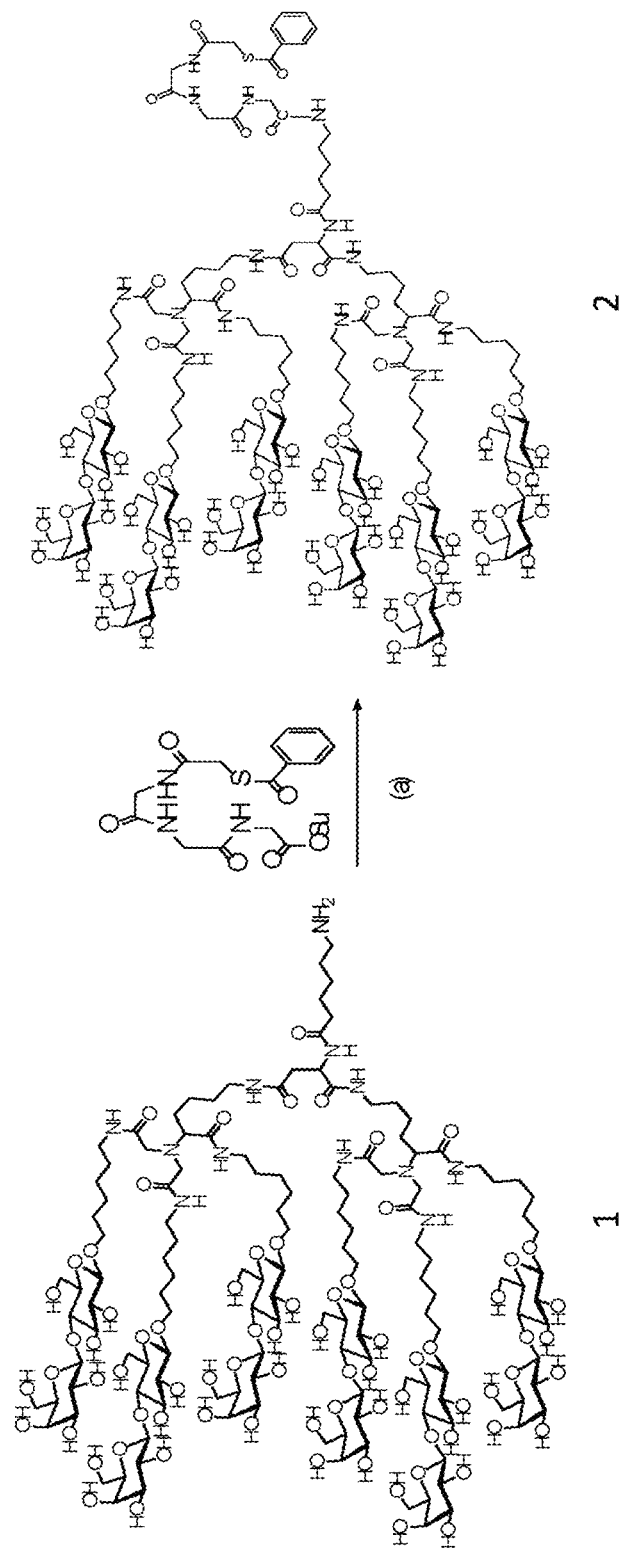
FIG. 6 is a flow chart of synthesizing $MAG_3$-hexa-lactose.

See FIG. 6 for the synthesis and preparation process of the $MAG_3$-hexa-lactose. The amino group exposed on the hexa-lactose obtained in Comparison example 2 and the carboxyl on S-benzoyl thioacetamide triglycine (S-Bz-$MAG_3$) are coupled. First, activate S-Bz-$MAG_3$ into mercaptoacetyltriglycine ($MAG_3$) through performing deprotection of benzoyl under the reaction condition of DCC/HOSu, and then add hexa-lactose and 4-dimethylaminopyridine obtained in Comparison example 2, so as to perform amide bonding to form $MAG_3$-hexa-lactose.

Comparison Example 4

Radio-Labelling Method of Tc-99m $MAG_3$-Hexa-Lactose

See Table 3 for the reaction condition of radio chemical labeling for Tc-99m $MAG_3$-hexa-lactose. As can be known from Table 3, for the radio-labelling of Tc-99m $MAG_3$-hexa-lactose, the optimal conditions are 20 ug of $MAG_3$-hexa-lactose, 1 m of Ci Tc-99m, 1 ug of $SnF_2$, 0.2 M of phosphate buffer solution (pH of 11), and reaction lasting 15 minutes at 60° C. In such a manner, the labelling yield reaches 79%, and the specific activity is $2\times10^9$ Bq/mg. Heating and purification are inconvenient for clinical applications.

TABLE 3

Analysis experiment of radio-labelling condition and radio chemical purity
(Radiochemical Purity) of Tc-99m MAG$_3$-hexa-lactose

| Buffer | pH | MAG$_3$-hexa-lactose | Na$^{99m}$TcO$_4$ (mCi of Tc-99m) | Reductant | Stabilizer | Temperature | RCP (%) |
|---|---|---|---|---|---|---|---|
| 0.2M NH$_4$OAc | 4 | 10 ug | 1 mCi | SnF$_2$ 1 ug | 7 ug/uL tartaric acid | Room temperature | 8 |
| 0.2M NH$_4$OAc | 8 | 10 ug | 1 mCi | SnF$_2$ 1 ug | 7 ug/uL tartaric acid | Room temperature | 63 |
| 0.2M NH$_4$OAc | 7.5 | 10 ug | 1 mCi | SnF$_2$ 1 ug | 7 ug/uL tartaric acid | Room temperature | 61 |
| 0.2M NH$_4$OAc | 7.5 | 10 ug | 1 mCi | SnF$_2$ 1 ug | 7 ug/uL tartaric acid | Room temperature | 61 |
| 0.2M NH$_4$OAc | 7.5 | 20 ug | 1 mCi | SnF$_2$ 1 ug | 7 ug/uL tartaric acid | Room temperature | 68 |
| 0.2M NH$_4$OAc | 7.5 | 50 ug | 1 mCi | SnF$_2$ 1 ug | 7 ug/uL tartaric acid | Room temperature | 28 |
| 0.2M phosphate | 11 | 20 ug | 1 mCi | SnF$_2$ 1 ug | 7 ug/uL tartaric acid | Room temperature | 71 |
| 0.2M phosphate | 11 | 20 ug | 1 mCi | SnF$_2$ 1 ug | 0 | Room temperature | 72 |
| 0.2M phosphate | 11 | 20 ug | 1 mCi | SnF$_2$ 1 ug | 0 | Room temperature 15 min | 71 |
| 0.2M phosphate | 11 | 20 ug | 1 mCi | SnF$_2$ 1 ug | 0 | 60° C. 15 min | 79 |
| 0.2M phosphate | 11 | 20 ug | 1 mCi | SnF$_2$ 1 ug | 0 | 60° C. 30 min | 51 |
| 0.2M phosphate | 11 | 20 ug | 1 mCi | SnF$_2$ 1 ug | 0 | 60° C. 60 min | 13 |
| 0.2M phosphate | 11 | 10 ug | 1 mCi | SnF$_2$ 1 ug | 0 ug ascorbic acid | Room temperature | 71 |
| 0.2M phosphate | 11 | 10 ug | 1 mCi | SnF$_2$ 1 ug | 2 ug ascorbic acid | Room temperature | 75 |
| 0.2M phosphate | 11 | 10 ug | 1 mCi | SnF$_2$ 1 ug | 5 ug ascorbic acid | Room temperature | 66 |
| 0.2M phosphate | 11 | 10 ug | 1 mCi | SnF$_2$ 1 ug | 10 ug ascorbic acid | Room temperature | 59 |

Comparison Example 5

Synthesis of DTPA-Tri-Galactosamine

Figure 7:
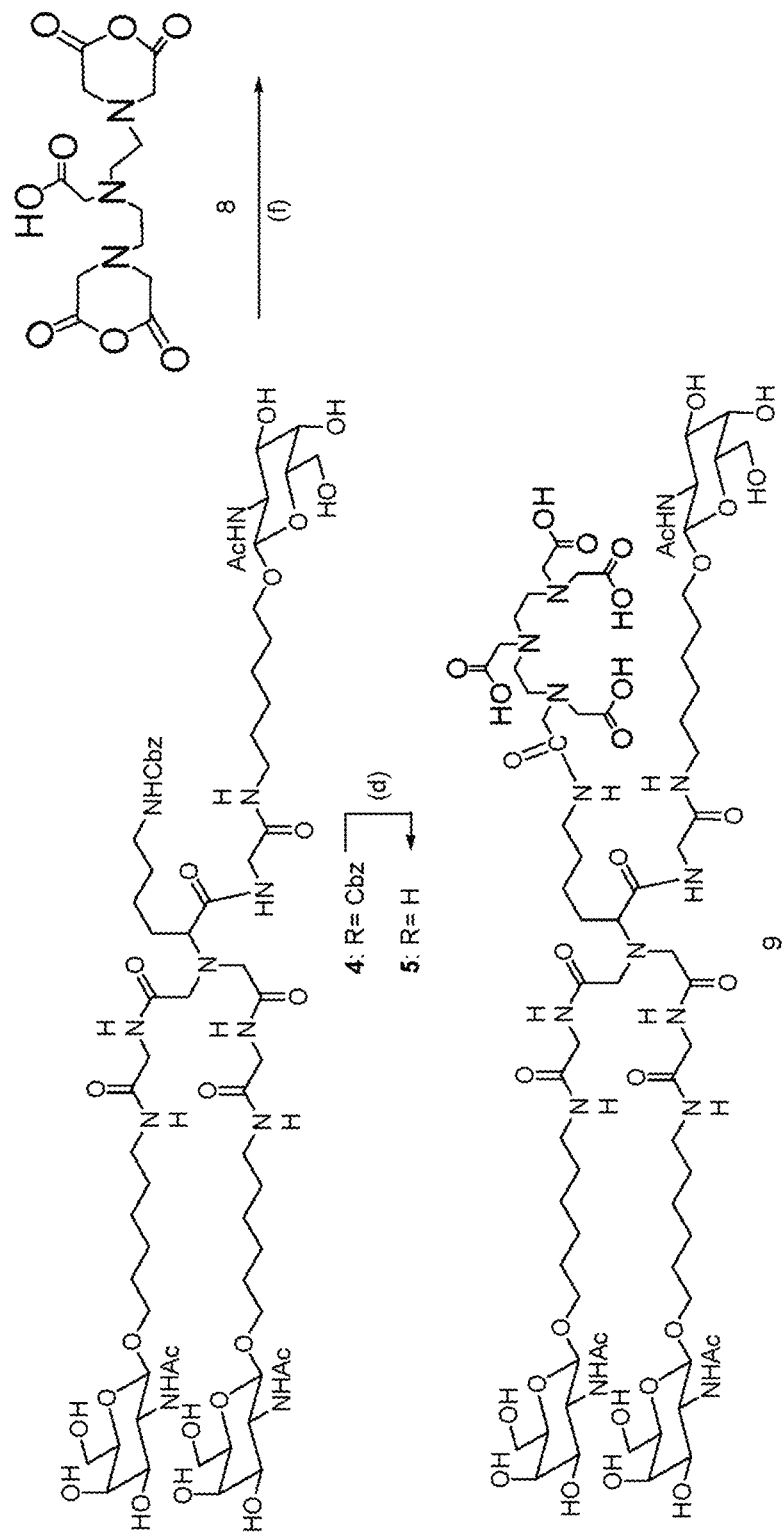
FIG. 7 is a flow chart of synthesizing DTPA-tri-galactosamine.

See FIG. 7 for the preparation process. Add diethylenetriamine pentaacetic dianhydride (DTPA dianhydride, 92.1 mg, 0.26 mmol) to tri-galactosamine (66.0 mg, 0.043 mmol) obtained in Embodiment 3 in the presence of 8% NaHCO$_3$ (aq) (2 mL) and mixing them evenly for 30 min at the room temperature. Add a second part of DTPA dianhydride (32.0 mg, 0.089 mmol) and mixing them evenly for 30 min at the room temperature. Add a third part of DTPA dianhydride (32.0 mg, 0.089 mmol) and mixing them evenly for 3 h at the room temperature. Perform neutralization with 1M of HCl to pH of from 7~8. Next, react the product in the bottle. Perform purification directly using an automatic fast preparative separation system. Adopt reverse column chromatography (Teledyne isco 150 gram RP-C18). The detection wavelength is set to be 214 nm. Perform gradient elution on the mobile phase for 12 minutes with A: methanol/B: 5% 50 mM of ammonium acetate methanol water solution at the flow speed of 26 milliliters per minutes from 5% to 60% A. After the separation and chromatography, perform collection at the product region and perform decompression and concentration (water bath at the temperature of 50° C.). Next, perform high vacuum drying for one day to obtain the final product (46 mg) of white solid DTPA-tri-galactosamine, where the yield is 56%. $^1$H NMR (300 MHz, D$_2$O) δ 4.31 (3H, d, J=6.9 Hz), 4.29 (3H, d, J=7.2 Hz), 3.83~3.71 (9H, m), 3.67~3.34 (37H, m), 3.26~3.06 (25H, m), 2.84 (2H, t, J=6.3 Hz), 1.49~1.37 (16H, m), 1.19 (14H, br); $^{13}$C NMR (75 MHz, D$_2$O) δ 178.32, 176.32, 174.42, 173.37, 173.15, 103.06, 102.20, 78.49, 75.48, 74.89, 74.59, 73.00, 72.67, 71.09, 70.69, 68.69, 66.47, 61.16, 60.24, 58.75, 58.53, 58.01, 56.08, 55.25, 51.75, 51.06, 50.33, 39.32, 39.16, 38.98, 28.84, 28.46, 26.01, 24.88, 24.82, 23.26; ESI-HRMS: calcd for 954.4451. found: m/z 954.4448 [M+2H]$^{+2}$.

Comparison Example 6

Synthesis of DTPA-Hexa-Lactose

Figure 8:
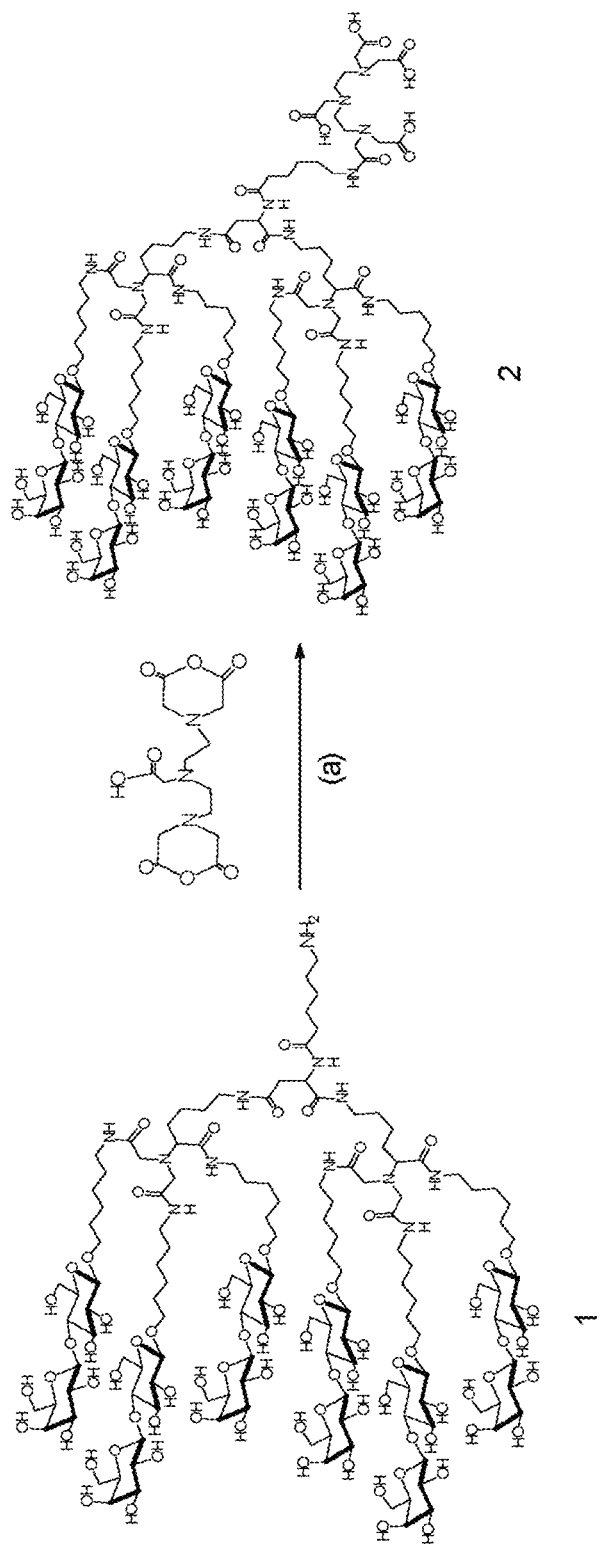
FIG. 8 is a flow chart of synthesizing DTPA-hexa-lactose.

See FIG. 8 for the preparation process. Add DTPA dianhydride (289 mg, 0.089 mmol) to hexa-lactose (445 mg, 0.135 mmol) obtained in Comparison example 2 in the presence of 8% NaHCO$_3$(aq) (2 mL) and mixing them evenly for 30 min at the room temperature. Add a second part of DTPA dianhydride (96 mg, 0.269 mmol) and mixing them evenly for 30 min at the room temperature. Add a third part of DTPA dianhydride (96 mg, 0.269 mmol) and mixing them evenly for 3 h at the room temperature. Perform neutralization with 1M of HCl to pH of from 7~8. Next, react the product in the bottle. Perform purification directly using an automatic fast preparative separation system. Adopt reverse column chromatography (Teledyne isco 150 gram RP-C18). The detection wavelength is set to be 214 nm. Perform gradient elution of the mobile phase for 12 minutes with A: methanol/B: 5% 50 mM of ammonium acetate methanol water solution at the flow speed of 26 milliliters per minute from 5% to 60% A. After separation and chromatography, perform collection at the product region and perform decompression and concentration (water bath at the temperature of 50° C.). Perform high vacuum drying for one day to obtain the final product of white solid DTPA-hexa-lactose (353 mg), wherein the yield is 72%. $^1$H NMR (300 MHz, $D_2O$) δ 4.45 (1H, t, J=6.9 Hz), 4.31 (6H, d, J=7.8 Hz), 4.29 (6H, d, J=7.5 Hz), 3.83~3.26 (88H, m), 3.18~2.97 (40H, m), 2.81 (2H, m), 2.54 (1H, dd, J=14.7, 6.0 Hz), 2.43 (1H, dd, J=14.7, 7.8 Hz), 2.12 (2H, t, J=6.6 Hz), 1.48~1.00 (66H, m); $^{13}$C NMR (75 MHz, $D_2O$) δ 179.06, 178.22, 176.79, 174.32, 174.04, 173.28, 172.34, 171.40, 103.06, 102.20, 78.49, 75.47, 74.88, 74.59, 72.98, 72.65, 71.08, 70.66, 68.68, 66.41, 61.15, 60.23, 59.07, 58.59, 58.48, 56.04, 52.00, 51.72, 51.59, 51.18, 50.89, 39.33, 39.20, 39.00, 28.86, 28.48, 28.23, 26.04, 25.81, 25.10, 24.91; and ESI-HRMS: calcd for 1217.5836. found: m/z 1217.5835 $[M+3H]^{+3}$.

Comparison Example 7

Radio-Labelling Method of Tc-99m-DTPA-Tri-Galactosamine

See Table 4 for the radio chemical label reaction condition of Tc-99m DTPA-tri-galactosamine. As can be known from Table 4, for the radio-labelling of Tc-99m DTPA-tri-galactosamine, the optimal conditions are 10 ug of DTPA-tri-galactosamine, 1 m of Ci Tc-99m, 1 ug of $SnF_2$, 0.2 M of $NH_4OAc$ (pH of 4), reacting for 15 minutes at the room temperature. In such a manner, the labelling yield reaches 70%, and the specific activity is $2 \times 10^9$ Bq/mg. Further purification is inconvenient for clinical applications.

TABLE 4

Analysis experiment of radio-labelling condition and radio chemical purity of Tc-99m DTPA-tri-galactosamine

| Buffer | pH | DTPA-triple-chain galactose amine | $Na^{99m}TcO_4$ (mCi of Tc-99m) | Reductant | Stabilizer | Temperature | RCP (%) |
|---|---|---|---|---|---|---|---|
| 0.2M $NH_4OAc$ | 4 | 10 ug | 1 mCi | $SnF_2$ 1 ug | 0 | Room temperature | 70 |
| 0.2M $NH_4OAc$ | 4 | 10 ug | 1 mCi | $SnF_2$ 1 ug | 0 | 60° C. 30 min | 70 |
| 0.2M $NH_4OAc$ | 4 | 10 ug | 1 mCi | $SnF_2$ 1 ug | 0 | 60° C. 1 h | 43 |

Comparison Example 8

Radio-Labelling Method of Tc-99m-DTPA-Hexa-Lactose

Weigh DTPA-hexa-lactose obtained in Comparison example 6 and place it into a V-shaped bottle. Add phosphate or ammonium acetate and dissolve the same. Weigh $SnF_2$ and dissolve the same in $H_2O$. Add 99 mTc-pertechnetate in the V-shaped bottle and then add the $SnF_2$ or $SnCl_2$ solution. Tighten the bottle cap and fill nitrogen and perform reaction at the room temperature. Table 5 shows that it cannot reach the radio chemical yield higher than 90%.

TABLE 5

Analysis experiment of radio-labelling condition and radio chemical purity of Tc-99m DTPA-hexa-lactose

| Buffer | pH | DTPA-hexa-lactose | Tc-99m | Reductant | Stabilizer | Temperature | RCP (%) |
|---|---|---|---|---|---|---|---|
| 0.2M $NH_4OAc$ | 6 | 100 ug | 0.1 mCi | $SnCl_2$ 0.2 ug | 0 | Room temperature | 43 |
| 0.2M $NH_4OAc$ | 6 | 100 ug | 0.1 mCi | $SnCl_2$ 0.2 ug | 0 | Room temperature | 83 |
| 0.2M $NH_4OAc$ | 6 | 1 ug | 0.1 mCi | $SnCl_2$ 0.2 ug | 0 | Room temperature | 30 |
| 0.2M $NH_4OAc$ | 6 | 5 ug | 0.1 mCi | $SnCl_2$ 0.2 ug | 0 | Room temperature | 69 |
| 0.2M $NH_4OAc$ | 6 | 10 ug | 0.1 mCi | $SnCl_2$ 0.2 ug | 0 | Room temperature | 80 |
| 0.2M $NH_4OAc$ | 4 | 1 ug | 0.1 mCi | $SnCl_2$ 0.2 ug | 0 | Room temperature | 63 |
| 0.2M $NH_4OAc$ | 6 | 1 ug | 0.1 mCi | $SnCl_2$ 0.2 ug | 0 | Room temperature | 30 |
| 0.2M $NH_4OAc$ | 4 | 100 ug | 0.1 mCi | $SnCl_2$ 0.2 ug | 0 | Rom temperature | 40 |

TABLE 5-continued

Analysis experiment of radio-labelling condition and radio chemical purity of Tc-99m DTPA-hexa-lactose

| Buffer | pH | DTPA-hexa-lactose | Tc-99m | Reductant | Stabilizer | Temperature | RCP (%) |
|---|---|---|---|---|---|---|---|
| 0.2M NH$_4$OAc | 4 | 100 ug | 0.1 mCi | SnCl2 0.04 ug | 0 | Room temperature | 84 |
| 0.2M NH$_4$OAc | 4 | 100 ug | 0.1 mCi | SnCl$_2$ 0.2 ug | 0 | Room temperature | 87 |
| 0.2 M NH$_4$OAc | 4 | 10 ug | 1 mCi | SnCl$_2$ 1 ug | 0 | Room temperature | 59 |
| 0.2M NH$_4$OAc | 4 | 10 ug | 1 mCi | SnCl$_2$ 2 ug | 0 | Room temperature | 46 |
| 0.2M NH$_4$OAc | 4 | 10 ug | 1 mCi | SnCl$_2$ 3 ug | 0 | Room temperoature | 28 |
| 0.2M NHP$_4$OAc | 4 | 10 ug | 1 mCi | SnF$_2$ 1 ug | 0 | Room temperature 30 min | 75 |
| 0.2M NH$_4$OAc | 4 | 10 ug | 1 mCi | SnF$_2$ 1 ug | 0 | 75° C. 30 min | 66 |

Experiment Example 1

Measure Radio Chemical Purity of Tc-99m Poly(ga)lactose (Amine) Using Radio Thin Layer Analysis Method The so-called "poly(ga)lactose (amine)" in the present invention means poly lactose or polygalactose amine.

The measurement of the radio chemical purity of poly(ga) lactose (amine) uses two sets of system developing solvents: (1) Use acetone as the developing solvent, and extract a small amount of reactant to perform radio-ITLC thin layer chromatography, in which only TcO$_4$⁻ runs to the solvent end, whose retention factor R$_f$=0.9~1.0, and Tc colloid and product Tc-poly(ga)lactose (amine) are retained at the original points, whose retention factors R$_f$=0~0.1. (2) Use acetonitrile solution of 50% as the developing solvent, and extract a small amount of reactant to perform radio-RP-TLC thin layer chromatography, in which TcO$_2$ is colloid that is still retained at the original point, and TcO$_4$⁻ and the product Tc-poly(ga) lactose (amine) turn to the solvent end, whose retention factor R$_f$=0.9~4.0. The calculation method of the radio chemical purity of Tc-99m-poly(ga)lactose (amine) is: (initial % in system 1)−(initial % in system 2).

Figure 9:
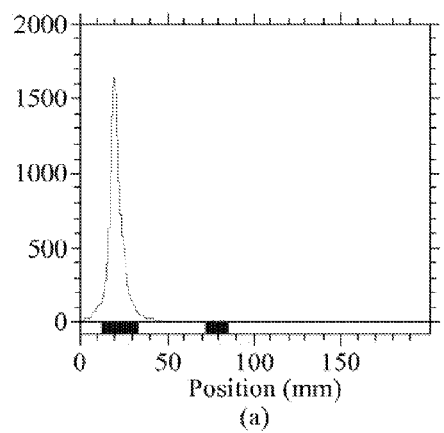
FIG. 9(a) is a fast thin layer chromatogram of a Tc-99m-$MAG_3$-tri-galactosamine radio chemical purity analysis system (1) with acetone being a developing solvent.
FIG. 9(b) is a fast thin layer chromatogram of a Tc-99m-$MAG_3$-tri-galactosamine radio chemical purity analysis system (2) with acetonitrile solution (50%) being a developing solvent.
Figure 9:
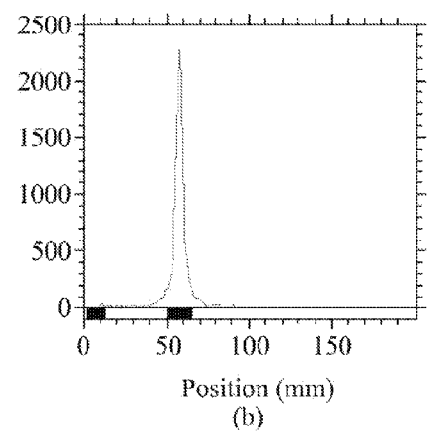

As shown in FIG. 9, by taking the developing phase as acetone, measure the radio chemical purity of the Tc-99m-MAG$_3$-tri-galactosamine, and it is measured that 1.18% of TcO$_4$⁻ activity exists at the position where the retention factor Rf=0.98, Tc-99m-MAG$_3$-tri-galactosamine and TcO$_2$ are left at the original points, which occupy 98.82%. When the developing phase is an acetonitrile solution of 50%, it is measured that 1.58% of TcO$_2$ exists at the original point. Therefore, the labelling yield this time is: 98.82%−1.58%=97.24%. That is, the radio chemical purity is greater than 97%. Measurement is performed for Tc-99m-MAG$_3$-tri-galactosamine by also adopting radio-high-performance liquid chromatography (RHPLC) in a reverse chromatography tube with the trifluoroacetic acid (TFA) of 0.05% and acetonitrile being the mobile phase solution. It is found that the retention time of Tc-99m MAG$_3$-Tris-galactosamine is 16.38 minutes. Accordingly, the Radio-ITLC thin layer chromatography can obtain the same result as the RHPLC, so that in the future the Radio-ITLC thin layer chromatography can be clinically used to perform analysis to evaluate the radio chemical purity rapidly.

Experiment Example 2

NanoSPECT/CT Image Analysis of Tc-99m-MAG$_3$-Tri-Galactosamine

Figure 10:
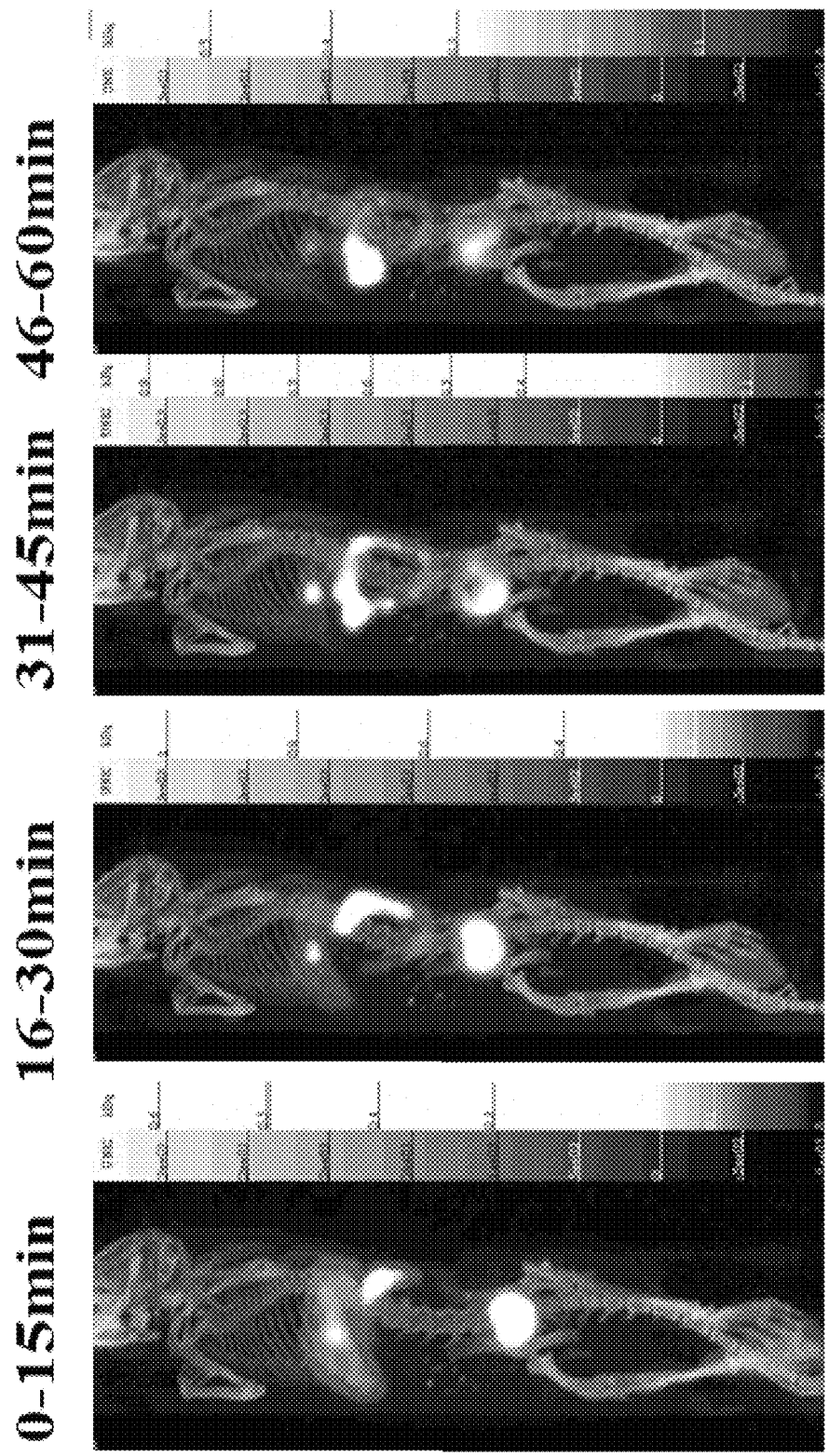
FIG. 10 is an imaging picture of Tc-99m-$MAG_3$-tri-galactosamine nanoSPECT/CT.

Inject Tc-99m-MAG$_3$-tri-galactosamine (20 nCi/g) in mice body through a tail vein. After injection, perform nanoSPECT/CT (Bio scan, Germany) immediately, perform imaging for 0-60 minutes with a multiple pinhole collimator, and perform nanoSPECT/CT image capturing and combination every 15 minutes. During imaging, the experiment animal is with isoflurane. The photographed images are shown in FIG. 10.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

To sum up, the present invention, in terms of the overall combination and features, has never appeared in the products of the same kind but also has never been published before the instant application. Therefore, the present application meets the requirements of the patent law, and thus the present application is filed for a patent according to the patent law.

What is claimed is:

1. A method for preparing Tc-99m-MAG$_3$-tri-galactosamine, comprising the following steps:
   (1) performing glycosidation reaction of acetylated galactose amine and 6-(benzyloxycarbonyl glycine amino) hexanol and performing deprotection of an acetoxy group on the galactose amine using alkali, so as to obtain 6-(benzyloxycarbonyl glycine amino) hexyl galactose amine;
   (2) performing hydrogenolysis reaction on the 6-(benzyloxycarbonyl glycine amino) hexyl galactose amine to obtain 6-(glycine amino) hexyl galactose amine;
   (3) reacting 6-(glycine amino) hexyl galactose amine and nitrilotriacetic acid protected by benzyloxycarbonyl amine to obtain tri-galactosamine;
   (4) performing amide bonding on the obtained tri-galactosamine and mercaptoacetyltriglycine (MAG$_3$) to cause reaction, so as to obtain MAG$_3$-tri-galactosamine; and (5) performing radio-labelling on the obtained MAG$_3$-tri-galactosamine and Tc-99m, so as to obtain Tc-99m-MAG$_3$-tri-galactosamine.

2. The method for preparing Tc-99m-MAG$_3$-tri-galactosamine according to claim 1, wherein the mercaptoacetyltriglycine (MAG$_3$) used in step (4) uses S-benzoyl thioacetamide triglycine precursor, and performs deprotection of benzoyl before reaction.

3. The method for preparing Tc-99m-MAG$_3$-tri-galactosamine according to claim 1, wherein step (5) is performed with SnHal2 (Hal represents chlorine or fluorine) serving as a reductant and a buffer solution at pH of from 10.0~12.

4. The method for preparing Tc-99m-MAG$_3$-tri-galactosamine according to claim 3, wherein SnHal$_2$ is SnF$_2$.

5. The method for preparing Tc-99m-MAG$_3$-tri-galactosamine according to claim 3, wherein the buffer solution is a phosphate buffer solution or ammonium acetate (NH4OAc).

6. The method for preparing Tc-99m-MAG$_3$-tri-galactosamine according to claim 4, wherein the buffer solution is a phosphate buffer solution or ammonium acetate (NH4OAc).

7. The method for preparing Tc-99m-MAG$_3$-tri-galactosamine according to claim 3, wherein step (5) is further performed with a stabilizer.

8. The method for preparing Tc-99m-MAG$_3$-tri-galactosamine according to claim 4, wherein step (5) is further performed with a stabilizer.

9. The method for preparing Tc-99m-MAG$_3$-tri-galactosamine according to claim 7, wherein the stabilizer is tartaric acid.

10. The method for preparing Tc-99m-MAG$_3$-tri-galactosamine according to claim 1, wherein the radio-labelling in step (5) comprising reaction lasting for 15 minutes without heating at the room temperature for yielding 97% radio-labelling rate with a specific activity of $3.7 \times 10^{10}$ Bq/mg.

* * * * *